(12) United States Patent
Gagnon

(10) Patent No.: US 6,321,605 B1
(45) Date of Patent: *Nov. 27, 2001

(54) SURFACE LOAD AND PRESSURE SENSING APPARATUS

(75) Inventor: Robert E. Gagnon, Mount Pearl (CA)

(73) Assignee: National Research Council of Canada, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/482,319

(22) Filed: Jan. 14, 2000

(51) Int. Cl.[7] .................................................. G01D 7/00
(52) U.S. Cl. ............................................ 73/862.046
(58) Field of Search ..................... 73/762, 862.041, 73/862.042, 862.043, 862.046

(56) References Cited

U.S. PATENT DOCUMENTS 3,987,668 * 10/1976 Propenoe ................................ 73/88
4,599,908 * 7/1986 Sheridan et al. .................. 73/862.04
4,644,801 * 2/1987 Kustanovich ..................... 73/862.04
4,901,584 * 2/1990 Bruner et al. ..................... 73/862.04
6,160,264 * 12/2000 Rebiere ............................ 250/559.22

* cited by examiner

Primary Examiner—Max Noori

(57) ABSTRACT

Apparatus for detecting loads applied to a surface, including a platen providing a continuous surface which is stiff relative to the loads being detected, a load receiving sheet extending over the platen surface and having an outer surface exposed to the loads, and, preferably, a layer of deformable material underlying the sheet and which is deformed when loads are applied to the sheet. A separator having regularly spaced apertures or gaps lies between the deformable layer and the platen surface, this being thin enough that loads to be measured applied to the outer surface of the sheet cause parts of the deformable layer to be pushed through the apertures or gaps into contact with the platen surface. The platen is preferably transparent, and a video camera is provided for viewing the platen surface and detecting areas where the deformable layer contacts the platen surface.

10 Claims, 6 Drawing Sheets

SURFACE LOAD AND PRESSURE SENSING APPARATUS

BACKGROUND OF THE INVENTION

1. Field of the Invention

The present invention relates to an opto-mechanical sensor for providing load and/or pressure distribution data, and especially to a pressure sensor providing high spatial resolution over a large area on a surface exposed to constant or varying forces. The system can provide large quantities of information in a visual and digital format using simple and easily implemented techniques. The sensor may have a large area, of several square meters, or a small area of less than one square centimeter. The pressures to be measured may also vary greatly.

2. Prior Art

Loads and pressure distributions on surfaces have traditionally been measured using mechanical load cells for the force on the whole surface and pressure sensors incorporated into the surface for local force and pressure measurement. The load cells are made of a material, usually metal, that deforms under load and the strain is monitored using an attached strain gauge. The pressure sensors are generally mechanical in design.

One type of pressure sensor is the piston/diaphragm design where load on the pressure head is transmitted through the piston to the diaphragm causing a deflection and a consequent change in output from a strain sensor on the diaphragm. Piezoelectric films are also available for measuring dynamic load and pressure. These existing technologies have drawbacks.

Firstly, the piston/diaphragm sensors require fairly extensive modification of the surface for installation and are limited in the number that can be installed so that large areas cannot be instrumented nor can the spatial resolution be very great because of structural modifications to the surface. Every sensor must have appropriate electrical connections which further limit the number and extent of the sensors on a surface.

Piezoelectric film has the advantage over piston sensors that the surface does not require much alteration and the spatial resolution can be high for the sensor spacing. The sensors can only be used for dynamic load situations however and there is still the issue of wiring being required for each of the sensing elements in a sensor array. They are impractical for coverage of large areas at high spatial resolution because of the demands on the data acquisition system. For example a one meter by one meter array of sensors with one centimeter spatial separation implies that there are 10,000 individual sensors from which to acquire data.

Surface-area transducers using electrical components such as capacitors to measure pressure distribution are also known, for example as described in U.S. Pat. No. 4,644,801 to Kustanovich, issued Feb. 24, 1987. Such transducers also require rather complex data acquisition systems.

U.S. Pat. No. 4,599,908 to Sheridan et al., issued Jul. 15, 1986, describes a system in which a pressure deformable body has an array of holes which are each aligned with a hole in a supporting base or platen, and each of the base or platen holes is fitted with the end of an optical fiber. The upper surface of the deformable body is covered by a load receiving flexible sheet, and when the flexible sheet is subjected to loads it causes the deformable body to bulge into its holes to reduce the hole diameter. The optical fibers are connected to a receiver viewed by a video camera, and the optical fibers transmit signals to the camera which indicate the reduction in hole diameter caused by the pressure. The Sheridan et al. system has drawbacks similar to those systems having a large number of load sensors, in that the fibers have to be attached individually to the holes, and a one meter by one meter array at one centimeter spacing would require 10,000 fibers. With less fibers, the resolution will be low. The need for a fiber connection corresponding to each hole also limits the nature of the deformable body; it needs an array of holes matching those of the base, which involves substantial expense, and cannot be formed as a body having a series of slits, as may be desirable for economy.

Other pressure distribution sensors use optical fibers in the plane of the sensors and which are sensitive to bending of the fibers or to contacts made between fibers when pressed together under pressure; an example is U.S. Pat. No. 4,901,584, issued to Brunner et al. on Feb. 20, 1990.

A pressure sensor is also known from U.S. Pat. No. 3,987,668, issued to Popenoe on Oct. 26, 1976. This uses a flexible light transmitting member which, under pressure, is pushed into contact with a light absorbing member; the area of contact between the light transmitting member and the light absorbing member is recognized by the frustration of internal reflection which occurs in this area. However, this sensor is only suitable for indicating overall pressure, and it is not suitable for showing pressure distribution since any area subjected to pressure affects neighbouring areas.

SUMMARY OF THE INVENTION

The present invention provides a load sensor arrangement which, as in Popenoe, uses the frustration of internal reflection or similar means to indicate contact between a transparent member and a non-transparent member. However, in the present invention the light transmitting member is separated from the light absorbing member by spacer means which divide the area subjected to pressure into an array of cells or zones which are effectively separate so that pressure distribution over a large area can be studied. Also, unlike in Popenoe, in the present invention the transparent member is generally a rigid platen, while the light absorbing member is the flexible member subjected to pressure.

Also, unlike some other prior art sensors referred to above, apparatus of this invention does not need optical fibers, and is capable of giving load sensing information at high spatial resolution, over a large area, at comparatively low cost as compared to the Sheridan et al. arrangement. In various forms of the invention it is capable of being monitored remotely either from the same side as the base or platen, i.e. opposite to that receiving the load or pressure, or from the same side as the pressure applying medium if this is transparent, for example if it is water or air, or from the edges of a thick platen having flat and clear edge surfaces. Since no optical fibers or similar cable means are required the base or platen may be isolated from the monitoring means. This may be useful for example where it is required to allow movement between the platen and the monitoring means or where the closeness of monitoring means to the platen would disrupt fluid flow.

In accordance with the invention, apparatus for sensing the load or pressure distribution on a surface comprises:

a platen providing a surface which is stiff relative to the loads being detected;

a load receiving sheet extending over the platen surface and having an outer surface exposed to the load or pressure; and separator means having regularly spaced apertures or gaps lying between the load receiving sheet and the platen and thin enough that loads to be detected applied to the outer surface of the load receiving sheet cause parts thereof, or parts of a sheet or layer underlying the load receiving sheet, to be pushed through the apertures or gaps and into contact with a platen surface. Areas of the load receiving sheet or of the underlying sheet or layer which contact the platen surface can be measured to indicate the pressure distribution.

Either the load receiving sheet is flexible so that it can be forced by pressure into the apertures of the separator, and/or it is provided with an underlying deformable layer which can contact the platen through the apertures. The apertures of the separator means effectively divide the area of the load receiving sheet into a series of cells or zones so that pressure or load on each such cell can be indicated.

One of the platen or load receiving sheet is a transparent member, and the apparatus preferably includes a video camera viewing the load receiving sheet or the underlying or deformable layer through the transparent member and detecting the area of contact between this sheet or layer and the platen surface.

The platen is usually a rigid sheet of transparent plastic material which constitutes the transparent member. Alternatively, instead of the platen being transparent, the load receiving sheet may be the transparent member, and the apparatus may include a video camera viewing an underlying layer through the transparent load receiving sheet and detecting increases in the areas of contact caused by loading of the sheet.

The platen may be a slab of transparent material having opposed edge surfaces which are flat and clear, the apparatus including a light source directing light into one of the edge surfaces at an angle providing total internal reflection at the surface of the platen where this is not in contact with the another surface. A video camera may view the light reflected by the deformable layer through a surface of the platen, or it may monitor, through an edge of the platen, those areas of the platen ilmer surface where the internal reflection of light is frustrated by contact between the sheet or the deformable layer and the platen. The latter system may be used where the only convenient access to the platen is through its edges.

BRIEF DESCRIPTION OF THE DRAWINGS

Preferred embodiments of the invention will now be described by way of example with reference to the accompanying drawings, in which;

FIGS. 6 and 7 are views of a preferred camera arrangement for the variation of FIG. 3a;

DETAILED DESCRIPTION.

Figure 1:
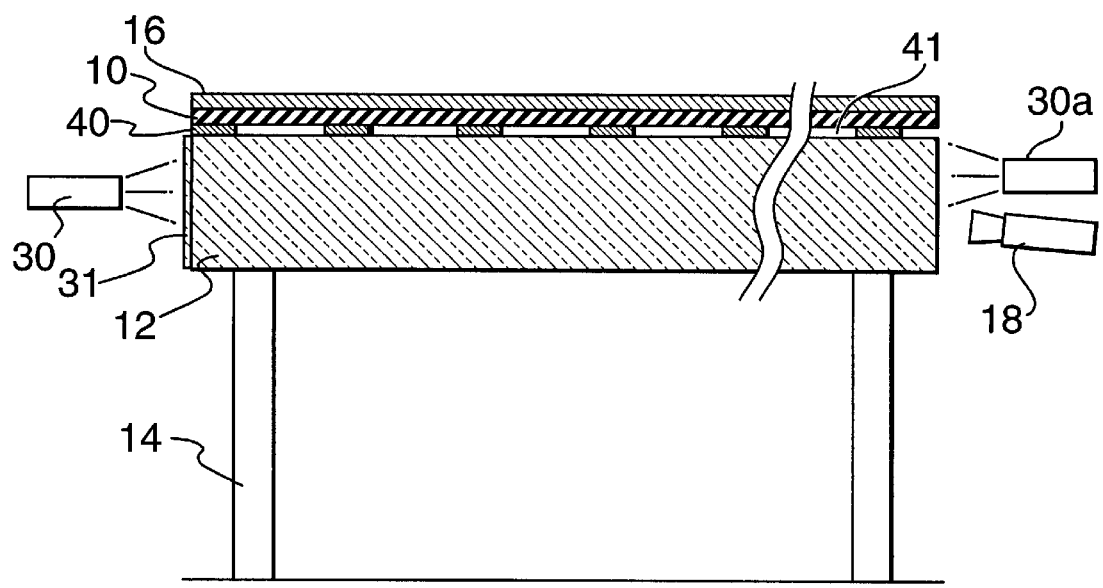
FIG. 1 shows a sectional view of a first embodiment of apparatus in accordance with the invention, using a deformable layer.
Figure 2A:
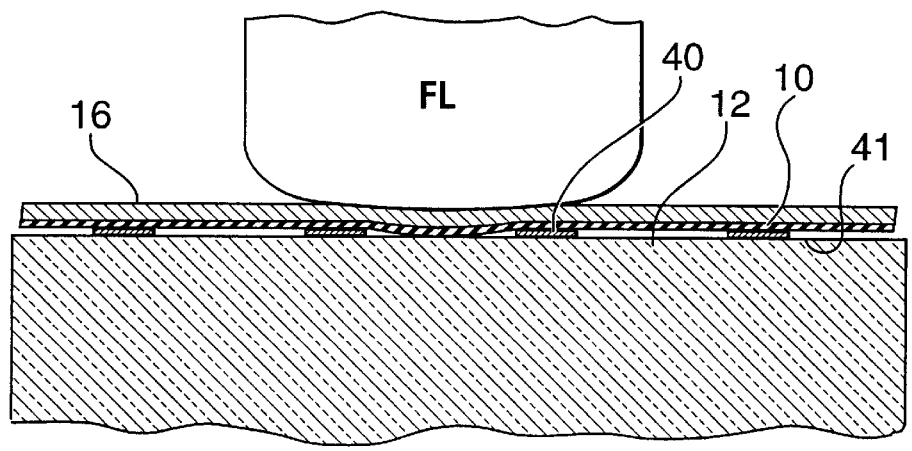
FIG. 2a is a detail of the deformable layer and adjacent parts when subjected to a flexible load.

FIGS. 1 and 2a show a first embodiment of the invention in which the sensing medium for the apparatus includes a deformable sheet or layer 10 underlying a flexible stainless steel load receiving sheet 16. The deformable layer 10 and load receiving sheet are supported on a rigid platen 12 formed as a slab of transparent flexible material such as "Plexiglas" (trademark). The slab needs to be rigid relative to the loads being measured. It is supported at its corners clear of a floor by legs 14.

The load receiving flexible sheet 16 extends over the platen and rests on top of the deformable layer; this is unapertured, unlike for example that used in the Sheridan et al. patent. In the unstressed condition it is separated from the platen 12 by a separator sheet 40 which is a sheet of thin material, for example of metal shim stock, about one-half the thickness of the deformable sheet. The sheet 40 has a regular array or grid of apertures 41, usually circular, occupying a major proportion of the area of the sheet. As indicated in FIG. 2a, which shows a flexible load FL, the sheet 40 is thin enough that the load to be measured can bend the load receiving sheet and the deformable material so that parts of it are pushed through the apertures 41 and into contact with the platen, and so that the area of contact between the deformable material and the platen gives an indication of the load or pressure, and of its distribution, applied to the top of sheet 16. Each aperture of the separator gives, in effect, a zone or area in which the load or pressure is measured, so that the number of different areas in which pressure is measured can be as large as the number of apertures in the separator.

The deformable sheet 10 is preferably rubber, which has sufficient flexibility for the purpose. Such a rubber sheet, when unapertured, has only a small amount of compressibility.

The amount of contact in each area or zone can be determined using camera and light means as shown in FIG. 1, where the camera 18 is mounted so as to view the light leaving the side 22 of the platen opposite to the light source 30, where the light from source 30 is diffused through a diffusing sheet 31. For this arrangement, the deformable sheet is preferably black or at least dark. Areas of the top of the platen in contact with air, viewed from the angle shown, behave as a mirror from which the light is reflected. However, wherever the deformable sheet makes contact with the platen the internal reflection becomes frustrated and the black deformable material gives a dark appearance.

The camera 18 is coupled to a computer which records the load measurements. Essentially, the optical sensing device, e.g. the CCD (charge-coupled device) chip of the video camera, serves as a high spatial resolution data acquisition system. Depending on the particular application, a regular video camera or a high speed video camera can be used. For example, a high speed camera with frame rates in the kHz range would be needed for dynamic events, such as ice impacts or indentation against structures, whereas slower events such as water wave and current loading on structures could be monitored using ordinary video equipment that acquires image fields at 60 Hz. Also, a still camera can be used to monitor static loads.

Instead of having light source 30 on the left hand side of the platen shining through the diffusing sheet 31, a light source as indicated at 30a may be used on the right hand side of the platen, shining through the platen onto a diffuse reflecting sheet similar to sheet 31 which then reflects light back onto the upper surface of the platen and into the camera 18. Having the light source at position 30a, i.e. on the same side as the camera, is convenient for saving space.

Another alternative light/camera arrangement which can be used with this embodiment is discussed below with reference to FIG. 3a.

Figure 2B:
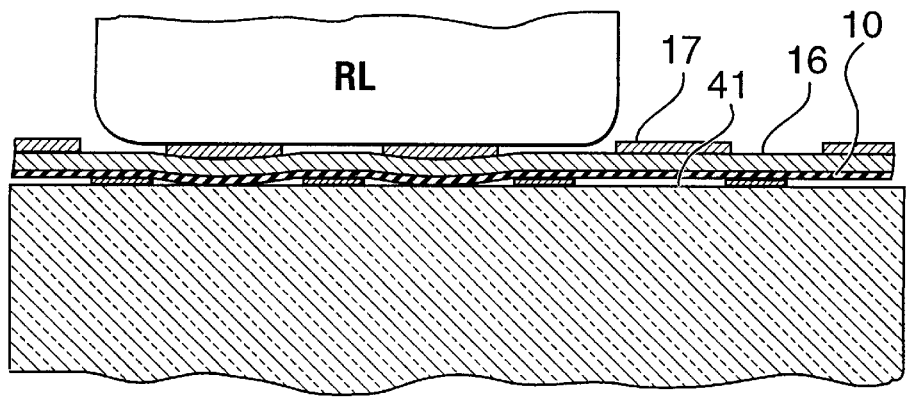
FIG. 2b is a view of parts similar to those shown in FIG. 2a, but using a different load receiving sheet suitable for a rigid load.

FIG. 2b shows a variation of the FIG. 2a arrangement for use with a rigid load RL, which, if applied to the arrangement of FIG. 2a, would tend to give different results depending on whether it were positioned centrally over one aperture or straddling two apertures. In the FIG. 2b arrangement, the load on the deformable sheet is concentrated above the areas of the apertures 41 by providing the upper surface of the load receiving sheet 16 with raised elements 17 positioned over the centers of the apertures, these raised elements being of substantially greater height than the thickness of the separator sheet so that the load remains clear of the main part of the deformable sheet when this is fully depressed.

An arrangment similar to FIG. 2b may form a simple load cell, by providing a plate extending over several of the raised elements 17.

Figure 2C:
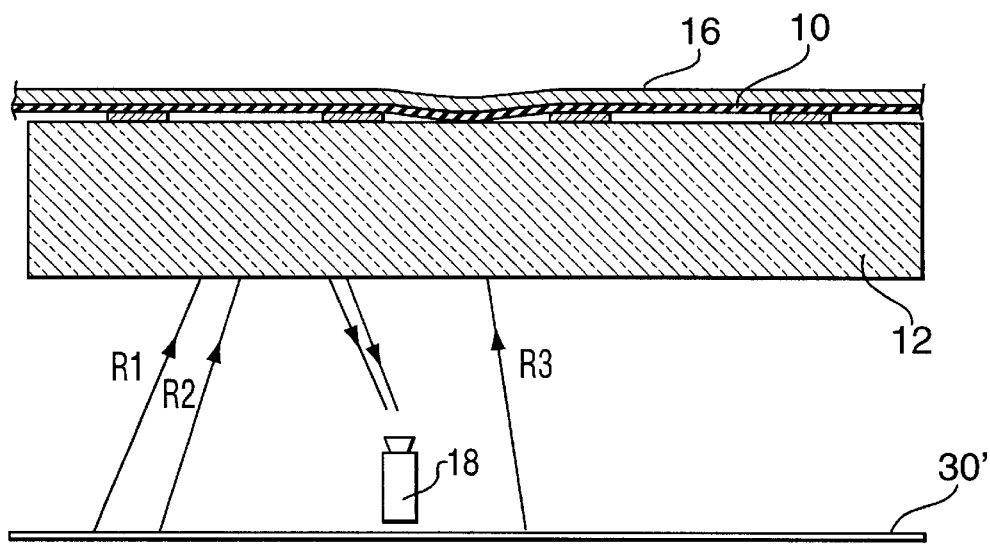
FIG. 2c is a view of an arrangement similar to FIG. 2b, but showing a further arrangement of light and detector.

FIG. 2c shows an arrangement similar to FIGS. 1 and 2a, but with a different light source/camera arrangement, which uses partial internal reflection of light, instead of total internal reflection as used in FIG. 1. Here, a sheet-form, diffuse light source 30' is situated underneath the transparent platen 12 and directs diffuse light upwards towards the top of the platen; source 30' may be a translucent sheet illuminated from below or a white sheet illuminated from above. The deformable sheet 10 is preferably black. Since the angle of incidence of the light is less than the critical angle required for total internal reflection, not all of the light is reflected from the upper internal surface of the platen, but nevertheless a substantial part is reflected into the camera 18 from areas which are in contact with the air, and which appear white. Sample light rays R1, R2 in FIG. 2c represent light which is reflected in this way. Where there is contact with the dark deformable sheet 10, as is the case for light ray R3, such areas appear dark.

Figure 3A:
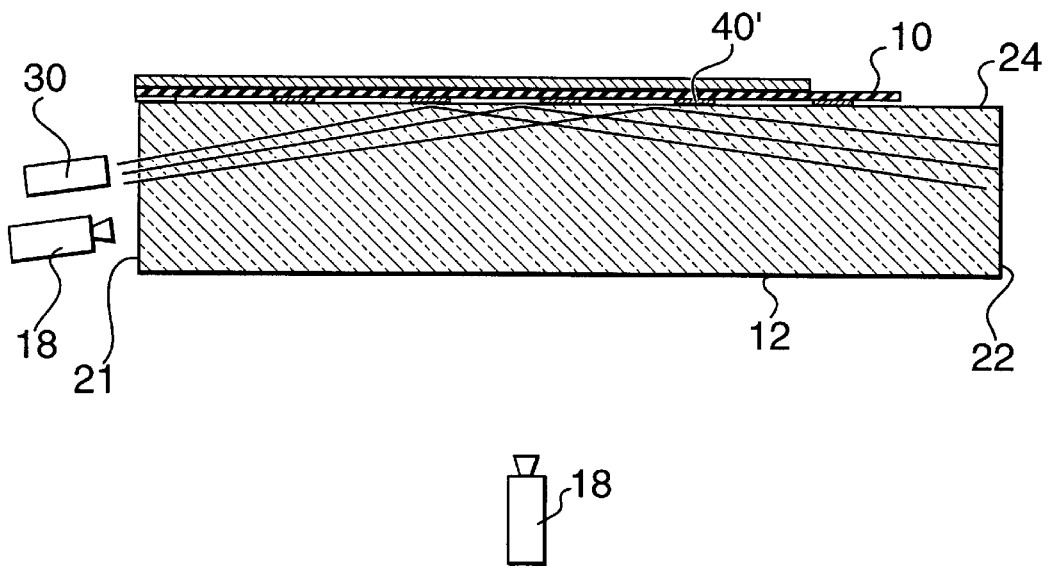
FIG. 3a is a view of the same arrangement as shown in FIG. 2a, showing different arrangements of associated light providing and viewing means.

FIG. 3a shows an arrangement which is similar to that of FIG. 2a, but in which the separator sheet is replaced by separator means in the form of a series of strips or tapes 40' which may be attached to the underside of the deformable sheet 10 or to the top of the platen 12. It is preferred that the deformable sheet be white or light in color. The platen here is a slab having opposed flat edge surfaces 21 and 22, and one of these surfaces receives light from a source 30 which is directed into the slab at a shallow upwards angle so as to meet the top surface 24 at a small acute angle such that, if the top surface is only in contact with air, the light is subject to total internal reflection and exits the opposed edge surface 22. Monitoring is done using a video camera 18 preferably mounted underneath the platen and viewing the top of the platen through its bottom flat surface. This camera sees darkness where the upper surface of the platen is in contact only with air, but where the platen is contacted by the light-colored deformable layer 10 this frustrates the total internal reflection and light is reflected into the camera. Hence, the amount of contact, and its variation with load, can be determined using the video camera 18.

An alternative position for the camera, viewing the deformable sheet from the same side surface 21 of the slab as the light source, is indicated at 18'. Again, this will see darkness except where the light colored tape or the rubber sheet frustrates the internal reflections and allows the camera to see the illuminated surface.

Figure 3B:
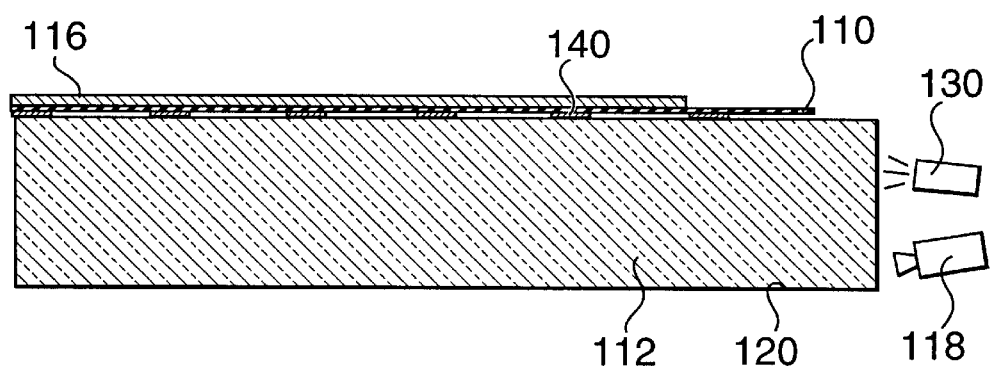
FIG. 3b is a view similar to that of FIG. 3a of another arrangement, in which a flexible sheet is used without a deformable body.

FIG. 3b shows a further variation in which no deformable sheet is used, and reliance is placed on a flexible load receiving sheet 116, separated from the platen 112 by a series of parallel strips 140 attached to the underside of the load receiving sheet. Strips of white tape 110 are also attached to the underside of the load receiving sheet between the strips 140, the tape strips 110 being of lesser thickness than the strips 140 so that the former are normally out of contact with the platen. When the sheet 116 is subjected to a flexible load, portions of the tape 110 are pushed into contact with the platen 112. While these portions of tape may be viewed in similar manner to that used for viewing parts of the deformable sheet in FIG. 3a, this figure shows an alternative position of the camera 118, wherein this is directed downwardly to receive light from light source 130 reflected off the lower internal surface 120 of the platen; with this arrangement the angular spread of the images of the strips is less steep than with the direct viewing in FIG. 3a. Instead of tape, the underside of the load receiving sheet may be suitably colored.

Figure 4:
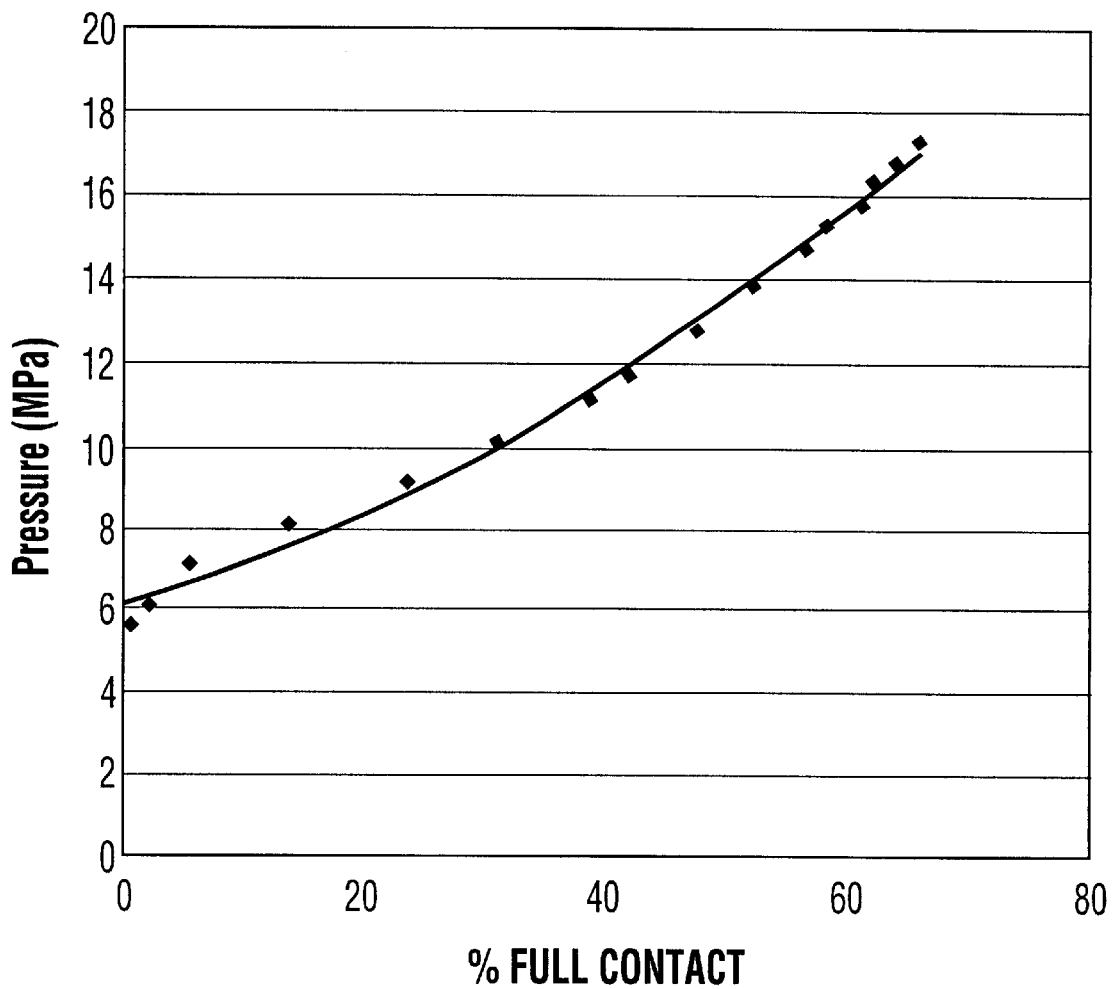
FIG. 4 is a calibration curve showing the relationship between measured pressure and percentage contact obtained for the configuration of FIG. 3b.

For the FIG. 3b arrangement, strips of tape 0.2 mm thickness and 3 mm wide, separated by 10 mm, were used with a stainless steel sheet 116 of 1 mm thickness, to measure pressure in the 5 to 25 MPa range. Tape 110 of thickness 0.15 mm was attached to the underside of the stainless steel sheet in the gap areas. FIG. 4 is a calibration curve showing the relationship between measured pressure and the percentage of full contact between the tape strips and the platen; this corresponding to the average percentage of contact over one unit pressure measurement area, defined as a 13 mm by 13 mm area.

Figure 5:
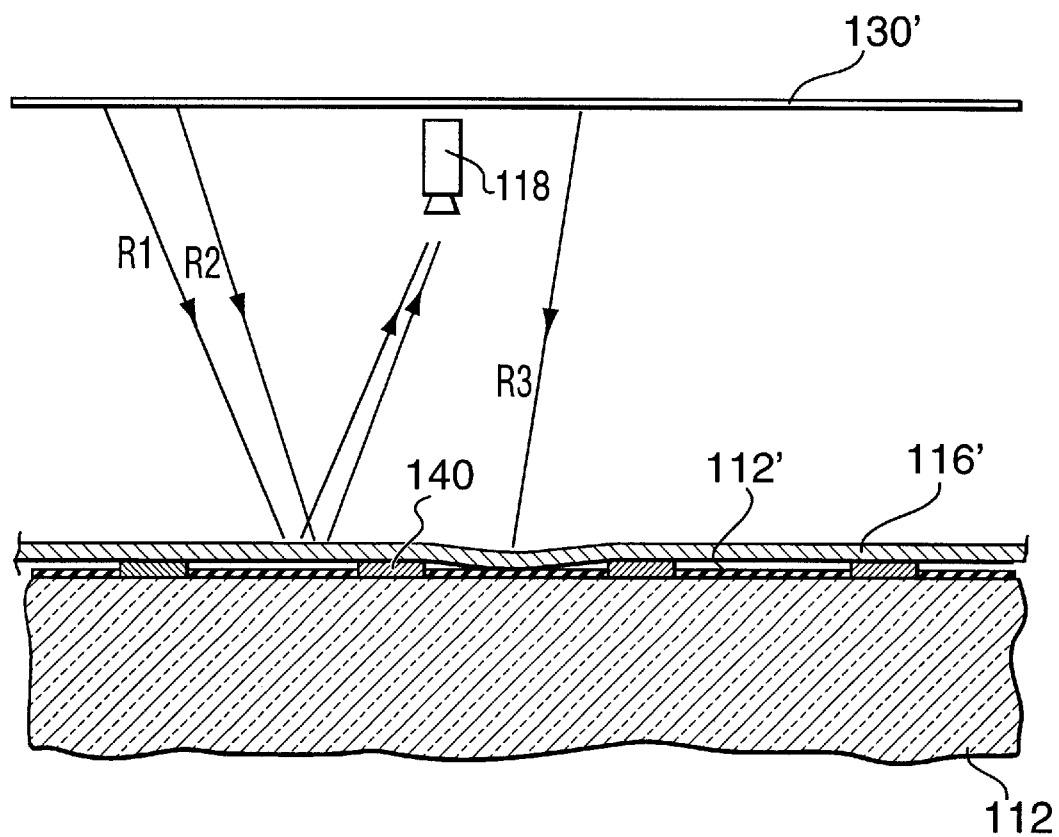
FIG. 5 is a view of an arrangement similar to that of FIG. 3b, but with a different arrangement of light and video camera.

FIG. 5 shows an embodiment similar to FIG. 3b but in which the platen is non-transparent, and a transparent load-receiving sheet 116' is used. Here, strips of black tape 112' lie flat on the platen 112 in the gaps between strips of the separator sheet 140. This tape is provided merely to give a black top surface for the platen, and here these strips effectively form the platen top surface. The separator strips 140 are higher than the strips of tape 112', so that contact between the load receiving sheet 116' and the tape 112' only occurs when the sheet is deformed by pressure as indicated. As in FIG. 2c, the light/camera arrangement uses partial internal reflection, but this time reflection is off the lower, inner surface of the sheet 116'. As in FIG. 2c, the light is provided by a diffuse light emitting sheet 130', and is reflected back into camera 118 wherever a gap is maintained under the sheet 116', such as is shown for light rays R1 and R2 in FIG. 5. The camera records dark areas where pressure causes the sheet to contact the black tape 112' and where reflection is frustrated, as shown for light ray R3. The light source 130' may be similar to the sourc 30' of FIG. 2c, i.e. a white translucent sheet illuminated from behind, or may be a diffuse sheet reflecting light from its lower surface; alternatively the light source may be difiuse ambient light including daylight or indirect room lighting.

Figure 6:
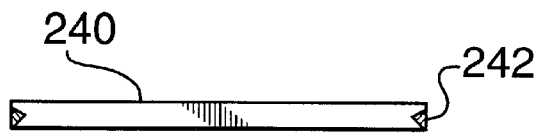
Figure 7:
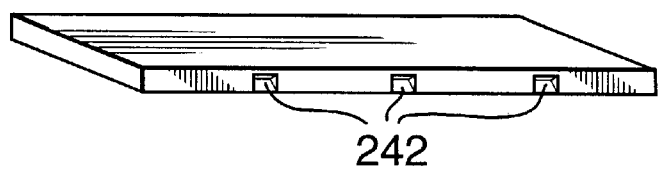
Figure 8:
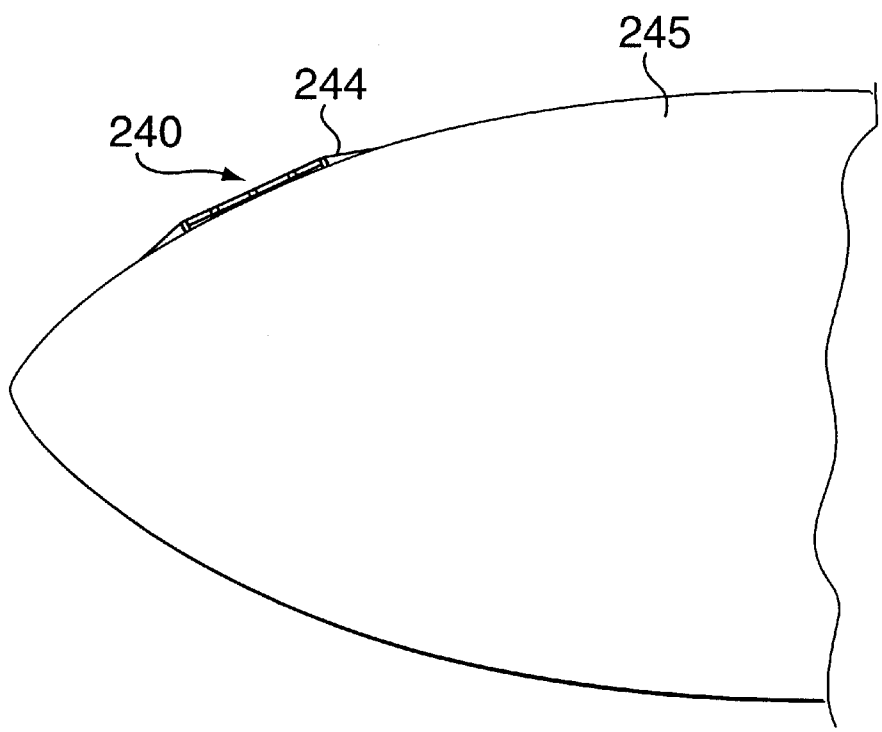
FIG. 8 shows a plan view of a ship bow having a sensor mounted thereon in accordance with the invention.

FIGS. 6, 7 and 8 show a practical application of the invention to measurement of pressure from ice on the bow of a ship. The embodiment is similar in principle to that of FIGS. 3b, and includes a platen/deformable sheet/load receiving sheet sensor unit indicated at 240, the opposite edges of which each have several recesses or ports 242 for receiving cameras which view the inner surface of the transparent platen on the side opposite to the load receiving side, as in FIGS. 3b, and which view the reflection of the outer surface of the platen caused by its total internal reflection in the bottom surface.

Hence the amount of contact, and its variation with load, can be determined visually using the video cameras. FIGS. 8 shows how a unit 240 can be mounted on the bow 245 of a ship to measure the ice pressure. The ends of the unit are held and protected by gussets 244, and the camera ports are fitted with small waterproof video cameras connected to electrical circuits within the hull by waterproof connections.

The advantages of the systems described are as follows:

1. Pressure data can be provided at high spatial resolution over a large area, of several square meters; the invention can also be used with small areas of less than one square centimeter;
2. The camera may be remote from the platen and sensing parts, but the direct viewing means that electrical connections, and electrical cross-talk, are eliminated; optical fibers are also not required;
3. It requires very simple materials and is easily fabricated;
4. It can be used for low or high pressure/load applications by the choice of suitable elastic properties and physical dimensions for the deformable sheet;
5. The data are acquired visually and in digital format and are therefore available immediately for visual and/or quantitative analysis.
6. Depending on conditions, the deformable sheet can be monitored from below the platen, above the platen, or from the platen edges where the faces of the platen are not accessible.

What is claimed is:

1. Apparatus for sensing loading applied to a surface, comprising:

a platen providing a continuous surface which is stiff relative to the loads being detected;

a load receiving sheet extending over the platen surface and having an outer surface exposed to said loads;

separator means having regularly spaced apertures or gaps lying between the load receiving sheet and the platen, said separator means being thin enough that loads to be detected applied to the outer surface of the load receiving sheet cause areas of the load receiving sheet or parts of an unapertured deformable underlying layer which underlies the load receiving sheet to be pushed through said apertures or gaps into contact with the platen surface, one of said platen or said load receiving surface being transparent, and said apparatus including means viewing a region of said load receiving sheet or the underlying layer through a surface of said transparent, member, which region has a plurality of said apertures or gaps, said viewing means detecting areas of said load receiving sheet or of said underlying layer which have been pushed into contact with the platen surface.

2. Apparatus according to claim 1, wherein said viewing means includes a video camera.

3. Apparatus according to claim 2, wherein the platen is a slab of transparent material having opposed flat edge surfaces, the apparatus including a light source directing light into one of said edge surfaces at an angle providing total internal reflection in areas not contacted by the load receiving sheet or the underlying layer.

4. Apparatus according to claim 3, wherein said video camera is positioned to view the load receiving sheet or the underlying layer where said sheet or layer contacts said platen surface.

5. Apparatus according to claim 2, wherein the platen is transparent, the apparatus including a diffuse light source directing light into the platen at an angle providing partial internal reflection in areas of the platen surface not contacted by the load receiving sheet or the underlying layer, said video camera being positioned to detect areas of the load receiving sheet or underlying layer where it contacts the platen surface and where the internal reflection of light is frustrated.

6. Apparatus according to claim 2, wherein the load receiving sheet is the transparent member, the apparatus including a diffuse light source directing light into the load receiving sheet at an angle providing partial internal reflection in areas of said sheet not contacted by the platen surface, said video camera being positioned to detect areas of the load receiving sheet where it contacts the platen surface and where the internal reflection of light is frustrated.

7. Apparatus for detecting loads applied to a surface, comprising:

a platen providing a continuous surface which is stiff relative to the loads being detected;

a load receiving sheet extending over the platen surface and having an outer surface exposed to said loads;

a layer of deformable material underlying the sheet and which is deformed when said loads are applied to the sheet;

separator means having regularly spaced apertures or gaps lying between the deformable layer and the platen surface, said separator means being thin enough that loads to be measured applied to the outer surface of the load receiving sheet cause parts of the deformable material to be pushed through said apertures or gaps into contact with the platen surface, said platen being transparent, and said apparatus including means viewing said platen surface and detecting areas where said deformable layer has been pushed into contact with the platen surface.

8. Apparatus according to claim 7, wherein the viewing means includes a video camera.

9. Apparatus according to claim 8, wherein the platen is a slab of transparent material having opposed flat edge surfaces, the apparatus including a light source directing light into one of said edge surfaces at an angle providing total internal reflection in areas not contacted by the deformable layer, and said video camera being positioned to view the deformable layer through an outer surface of the platen in areas where the deformable layer frustrates total internal reflection of the light.

10. Apparatus according to claim 1, wherein said load receiving sheet has raised elements overlying said gaps or apertures in the separator means.

* * * * *